United States Patent [19]

Carstensen

[11] 4,185,085

[45] Jan. 22, 1980

[54] DIFFERENTIAL DIAGNOSTIC SPERM EXAMINATION

[75] Inventor: Carsten A. Carstensen, Heuchelheim, Fed. Rep. of Germany

[73] Assignee: Boehringer Mannheim GmbH, Mannheim, Fed. Rep. of Germany

[21] Appl. No.: 842,003

[22] Filed: Oct. 13, 1977

[30] Foreign Application Priority Data

Nov. 9, 1976 [DE] Fed. Rep. of Germany ....... 2651060

[51] Int. Cl.² ......................... G01N 1/30; G01N 21/60
[52] U.S. Cl. ............................................. 424/3; 8/18; 435/2; 424/7
[58] Field of Search ................. 424/3, 7; 195/1.7, 1.8; 117/124 D; 8/18

[56] References Cited

U.S. PATENT DOCUMENTS

| | | | |
|---|---|---|---|
| 3,796,594 | 3/1974 | Thomas | 424/3 X |
| 3,906,120 | 9/1975 | Geating | 424/3 X |
| 4,070,495 | 1/1978 | Berger | 424/3 |

OTHER PUBLICATIONS

Isenberg, Vet. Bull., vol. 20, 1950, Ab. No. 3420.
Hancock, Vet. Bull., vol. 23, 1953, Ab. No. 3205.
Rollinson, Vet. Bull., vol. 23, 1953, Ab. No. 744.
Farrelly, Vet. Bull., vol. 27, 1957, Ab. No. 3747
Wintrobe, Clinical Hematology, Lea & Febiger, Phila., 2nd Ed. Revised, 1949, pp. 272, 273, 276–279.
Sabin, Bull. The Johns Hopkins Hosp., vol. 34, 1923, pp. 277–288 & plate.
Farrelly, Irish Vet. J., 1957, pp. 2–18.
Rollinson, Brit. Vet. J., vol. 107, 1951, pp. 451–468.
Rollinson, Brit. Vet. J., vol, 107, 1951, pp. 258–273.
Rollinson, Brit. Vet. J., vol. 107, 1951, pp. 203–214.
Isenberg, AJCP, vol. 18, 1948, p. 94.
Hancock, J. Exp. Biol., vol. 30, 1953, pp. 50–56.

*Primary Examiner*—Anna P. Fagelson
*Attorney, Agent, or Firm*—Sprung, Felfe, Horn, Lynch & Kramer

[57] ABSTRACT

A method of differential diagnostic sperm examination and the use of prestained slides in that method comprising placing the specimen to be examined on a prestained blood-picture slide, developing the stain and examining same thereafter.

2 Claims, 1 Drawing Figure

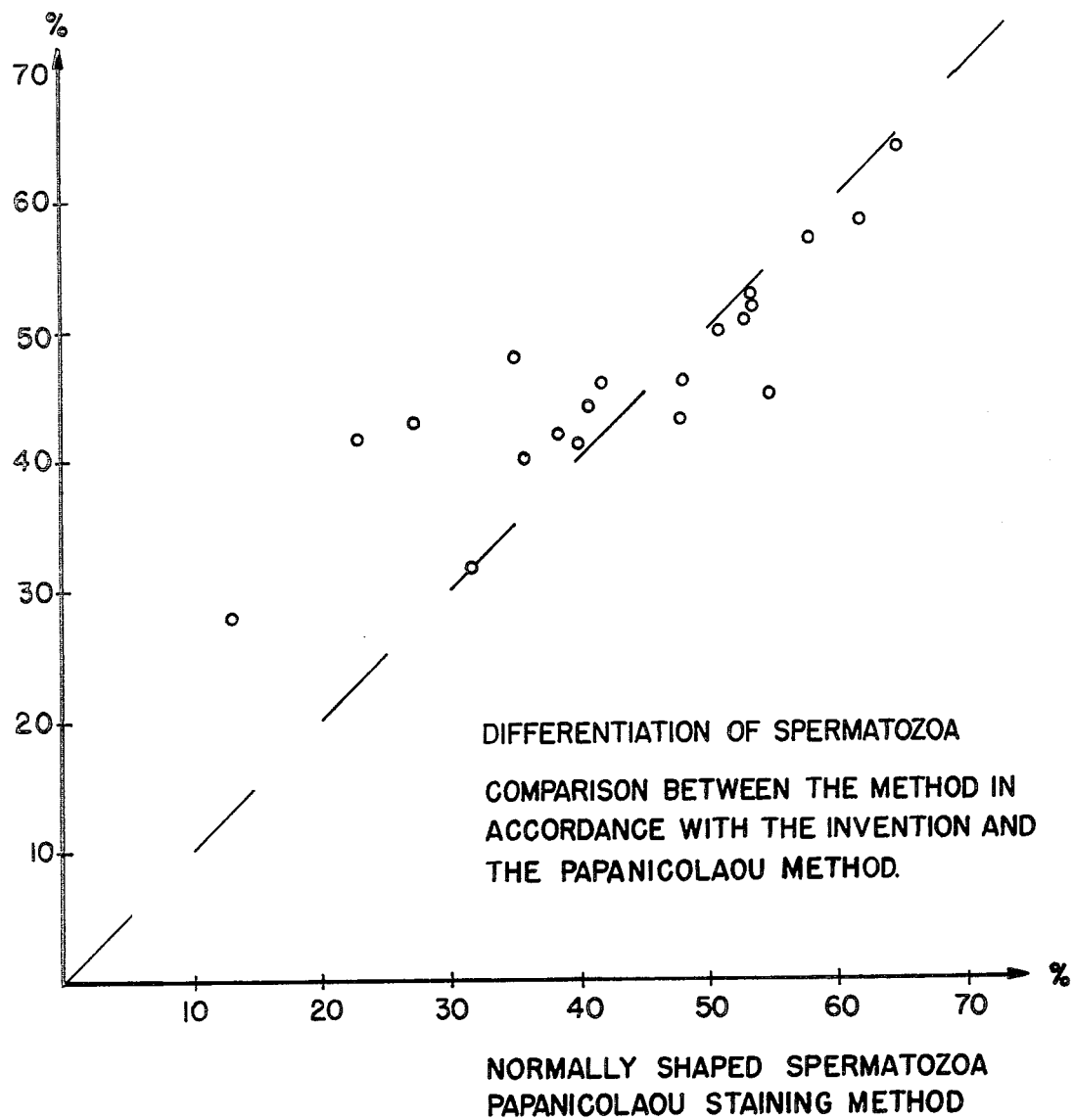

DIFFERENTIAL DIAGNOSTIC SPERM EXAMINATION

BACKGROUND OF THE INVENTION

The present invention relates to an improved method of differential diagnostic sperm examination and the use of prestained slides in the employment of that method.

The principal components of sperm are the spermatozoa and the round cells, which in turn are made up of leukocytes and the cells of the spermiogenesis. The morphological examination of spermatozoa is of great importance in andrology. Differentiation between normal and pathological sperms yields useful information in fertility examinations. Precise differentiation of these normal and pathological forms under the microscope is possible only when the sperms have been prestained. A number of staining methods have been developed (such as the Mayer-Stiasny method and the Papinicolaou method), but they are usually very complicated in practice.

Thus, in the Papanicolaou method (see C. Schirren, Praktische Andrologie, Berlin 1971, page 20), for example, the smears are air-dried for 24 hours and then fixed for 5 minutes in a 1:1 mixture of 95% alcohol and ether. The smears are then subjected to an extensive treatment which comprises the following successive steps:

Immersion for 10 sec each in a descending alcohol series (80%, 70% and 50%);

10 sec in distilled water;

3 min in a hematoxylin solution; 10 min or longer in running water; 2 sec in 0.5% hydrochloric acid; 5 min in running water; 10 sec each in an ascending alcohol series (50%, 70%, 80% and 95% ethanol);

2 min staining in Orange G solution; 5 sec in 95% ethanol; 2 min staining in Polychrome ea 65 solution; 5 sec each rinsing off the excess dye in three different vessels, each time with 95% ethanol;

2 min immersion in absolute alcohol;

2 min immersion in a 1:1 mixture of absolute alcohol and xylol; and 20 min in xylol.

This prescription obviously is very complicated and time-consuming and can be followed only by trained laboratory personnel.

The problem thus was to find a much simpler and less time-consuming method for differential diagnostic sperm examination that could be carried out even by untrained laboratory personnel.

SUMMARY OF THE INVENTION

It has now been found, quite unexpectedly, that the morphological properties of sperms can be shown in an outstanding manner when one drop of ejaculate is placed on prestained blood-picture slides, as described, for example, in U.S. Pat. No. 4,070,495, capped with a cover glass, and examined microscopically after the stain has developed. The sperms then show up in a high-contrast coloration while the background remains colorless.

In order to obtain good, reliable results, it is advisable to allow at least 30 minutes for the stain to develop. A period ranging from one to two hours has been found to be particularly advantageous. If only a cursory determination is to be made, the microscopic examination may begin after a waiting time of just 5 to 10 minutes.

Spermatozoa exhibit the following color differentiations:

Within the heads, the nucleus is stained dark purple. Depending on the focus, the plasma ranges from orange to light violet. With pathological enlargement, the middle also appears light violet while the tail is stained only weakly but is clearly visible. This kind of staining permits excellent differentiation of the various normal and pathological shapes of spermatozoa.

Of the round cells, the leukocytes are stained as described in U.S. Pat. No. 4,070,495 namely: A purple nucleus and, depending on the type of leukocytes, almost colorless, yellow or orange-red plasma.

In the case of the cells of the spermiogenesis (spermatogonia, spermatocytes and spermides), the nuclei are stained dark purple and the plasma light violet, as with the spermatozoa, so that they are readily distinguished from the leukocytes on the basis of their morphology.

The method in accordance with the invention thus offers the following significant advantages amount to an advance in the art over conventional staining methods:

24-hour air drying, usual up to now, may be dispenses with so that the differential diagnostic sperm examination may be performed the same day.

Development of the staining usually requires a waiting time of not more than 30 to 120 minutes rather than about one hour's work with numerous manipulations.

Staining itself is extremely easy to do and may be done even by unskilled personnel. Differentiation by the physician, too, is simple and straightforward.

It has surprisingly been found that by comparison with the conventional Papanicolaou staining method, the method in accordance with the invention— permits better or at least equally good differentiation between normal and pathological sperms, and minimizes the risk of deformation, and hence the number of shapes which erroneously might be regarded as pathological.

BRIEF DESCRIPTION OF THE DRAWING

The FIGURE is a graph of the results from the use of the method of the present invention in comparison to the prior art.

DETAILED DESCRIPTION OF THE INVENTION

The invention will be explained in greater detail in terms of the following examples:

EXAMPLE 1

Prestained slides usable in accordance with the invention may be prepared by the method described in U.S. Pat. No. 4,070,475.

To this end, the following solution is prepared by the use of appropriately purified dyes:

Methylene blue N-hydrochloride: 130 mg p0 Cresyl violet acetate: 270 mg

Methanol: up to 100 ml

This solution is sprayed from an 0.5 mm broad-spray nozzle (SS 60 67228-45 of Spraying Systems) with a spraying angle of about 25 degrees from a distance of 20 cm through a mask in a width of 3 cm onto slides which are passed under the nozzle at a speed of 1.5 meters per minute. Methylene blue N is defined in U.S. Pat. No. 4,070,475 as New Methylene Blue, C.I. Basic Blue 24 and 3,7-bis-(N-ethylamino)-2,8-dimethylphenothiazonium chloride.

Spraying pressure: 1.2 atm gauge. Flow rate through the nozzle: 10 ml/min.

With an average drop size of about 20μ, the quantity of dye applied is about 3 μg/cm².

A drop of liquefied ejaculate is applied to a prestained slide so prepared by means of a plantinum-wire loop 3 mm in diameter and capped with a cover glass. After about 30 to 120 minutes, the staining is evaluated under the microscope with about 1000X magnification by the use of an oil-immersion objective.

Examined ten times, an ejaculate having a high proportion of normal shapes showed good agreement with the Papanicolaou staining method:

74±3% (standard-deviation, $s_D$) normal spermatozoa by the method of determination in accordance with the invention as against 73±2% by the Pananicolaou method.

EXAMPLE 2

An ejaculate having relatively few normal shapes was examined in the manner described in example 1. Here it was found that in the Papanicolaou method the normal shapes are underestimated. This is evidently due to a deformation of the cells by the staining method after Papanicolaou, which is more of a factor when the proportion of normal shapes is small than when it is large: 40±3% normal sperms by the method in accordance with the invention as against 33±5% by the Papanicolaou method.

EXAMPLE 3

20 Ejaculates having different proportions of normally shaped spermatozoa were examined both by the method in accordance with the invention, as described in example 1, and by the Papanicolaou method. In keeping with the results obtained in examples 1 and 2, values that were in agreement were obtained by both methods when there was a high proportion of normal shapes whereas the method in accordance with the invention yielded higher values than the Papanicolaou method when the proportion of normal shapes was low. The results are plotted in the FIGURE.

What is claimed is:

1. A method for differential diagnostic sperm examination, comprising placing the specimen to be examined on a prestained blood-picture slide wherein the dye component of the prestained slide contains chromatographically pure new methylene blue and cresyl violet acetate in a ratio ranging from 1:1.5 to 1:5, developing the stain and examining same thereafter.

2. Method as defined in claim 1, wherein the developing time for the staining is from 5 to 120 minutes.

* * * * *

UNITED STATES PATENT AND TRADEMARK OFFICE
CERTIFICATE OF CORRECTION

PATENT NO. : 4,185,085
DATED : Jan. 22, 1980
INVENTOR(S) : Carsten Andreas Christensen It is certified that error appears in the above-identified patent and that said Letters Patent are hereby corrected as shown below:

Col. 2, line 57, should read:

Methylene blue N-hydrochloride      130 mg.

Col. 2, line 58, should read:

Cresyl violet   acetate      270 mg

Signed and Sealed this

Eighth Day of July 1980

[SEAL]

Attest:

Attesting Officer

SIDNEY A. DIAMOND
Commissioner of Patents and Trademarks